(12) United States Patent
Giles et al.

(10) Patent No.: US 9,576,777 B2
(45) Date of Patent: Feb. 21, 2017

(54) MULTI-DIMENSIONAL SURVEY SCANS FOR IMPROVED DATA DEPENDENT ACQUISITIONS

(71) Applicant: Micromass UK Limited, Wilmslow (GB)

(72) Inventors: Kevin Giles, Stockport (GB); Jason Lee Wildgoose, Stockport (GB)

(73) Assignee: Micromass UK Limited, Wilmslow (GB)

( * ) Notice: Subject to any disclaimer, the term of this patent is extended or adjusted under 35 U.S.C. 154(b) by 0 days.

(21) Appl. No.: 14/386,355

(22) PCT Filed: Mar. 11, 2013

(86) PCT No.: PCT/GB2013/050595
§ 371 (c)(1),
(2) Date: Sep. 19, 2014

(87) PCT Pub. No.: WO2013/140132
PCT Pub. Date: Sep. 26, 2013

(65) Prior Publication Data
US 2015/0041636 A1  Feb. 12, 2015

(30) Foreign Application Priority Data
Mar. 22, 2012 (GB) .................. 1205009.2

(51) Int. Cl.
*H01J 49/40* (2006.01)
*H01J 49/00* (2006.01)
(Continued)

(52) U.S. Cl.
CPC ........ *H01J 49/0031* (2013.01); *G01N 27/624* (2013.01); *H01J 49/004* (2013.01); *H01J 49/40* (2013.01); *G01N 30/72* (2013.01)

(58) Field of Classification Search
None
See application file for complete search history.

(56) References Cited

U.S. PATENT DOCUMENTS 6,323,482 B1 * 11/2001 Clemmer ............. G01N 27/622
250/282
6,498,342 B1  12/2002 Clemmer
(Continued)

FOREIGN PATENT DOCUMENTS

GB  2443952 A * 5/2008 ........... G01N 27/622

OTHER PUBLICATIONS

Cherokee et al. "Ion Trap/Ion Mobility/Quadrupole/Time-of-Flight Mass Spectrometry for Peptide Mixture Analysis", Analytical Chemistry, vol. 73, No. 2, Jan. 1, 2001.*
(Continued)

*Primary Examiner* — Michael Logie
(74) *Attorney, Agent, or Firm* — Diederiks & Whitelaw, PLC (57) ABSTRACT

A method of analyzing ions is disclosed comprising performing an initial multi-dimensional survey scan comprising separating parent ions according to a first physico-chemical property (e.g. ion mobility) and then separating the parent ions according to a second physico-chemical property (e.g. mass to charge ratio). A plurality of parent ions of interest are then determined from the initial multi-dimensional survey scan. Once parent ions of interest have been determined, the plurality of parent ions of interest are sequentially selected based upon the first and second physico-chemical properties during a single cycle of separation. The parent ions of interest may then be fragmented and corresponding fragment ions may then be mass analyzed.

28 Claims, 3 Drawing Sheets (51) Int. Cl.
*G01N 27/62* (2006.01)
*G01N 30/72* (2006.01)

(56) References Cited

U.S. PATENT DOCUMENTS

| | | | | |
|---|---|---|---|---|
| 7,451,052 | B2 | 11/2008 | Wang et al. | |
| 7,586,088 | B2* | 9/2009 | Bateman | H01J 49/004 250/281 |
| 8,076,637 | B2 | 12/2011 | Pringle et al. | |
| 8,101,910 | B2 | 1/2012 | Loboda | |
| 8,129,674 | B2 | 3/2012 | Ogata et al. | |
| 8,530,831 | B1 | 9/2013 | Coon et al. | |
| 8,766,172 | B2 | 7/2014 | Gorenstein et al. | |
| 9,012,840 | B2 | 4/2015 | Bateman et al. | |
| 9,190,251 | B2* | 11/2015 | Green | H01J 49/0031 |
| 2008/0048109 | A1* | 2/2008 | Schwartz | H01J 49/0031 250/282 |
| 2008/0185511 | A1* | 8/2008 | Senko | H01J 49/423 250/283 |
| 2010/0084547 | A1* | 4/2010 | Pringle | H01J 49/428 250/282 |
| 2010/0108879 | A1 | 5/2010 | Bateman et al. | |
| 2010/0237236 | A1 | 9/2010 | Thomson et al. | |
| 2013/0277548 | A1* | 10/2013 | Claude | H01J 49/0027 250/282 |
| 2013/0297226 | A1* | 11/2013 | Wang | H01J 49/0036 702/23 |
| 2014/0048701 | A1 | 2/2014 | Green et al. | |
| 2014/0131567 | A1* | 5/2014 | Makarov | H01J 49/004 250/283 |
| 2014/0339416 | A1* | 11/2014 | Vidal-de-Miguel | H01J 49/004 250/282 |

OTHER PUBLICATIONS

Koeniger et al., "AN IMS-IMS Analogue of MS-MS", Anal. Chem. 2006.*

Baker et al.,"*An LC-IMS-MS Platform Providing Increased Dynamic Range for High-Throughput Proteomic Studies*", Journal of Proteome Research, vol. 9, No. 2, pp. 997-1006, 2010.

Coy et al., "*DMS-Prefiltered Mass Spectrometry for the Detection of Biomarkers*", Proceedings of SPIE, vol. 6954, pp. 695411-695411-10, 2008.

Harvey et al., "*Ion Mobility Mass Spectrometry for Peptide Analysis*", Methods of Academic Press, vol. 54, No. 4, pp. 454-461.

Hoaglund et al.,"*Coupling Ion Mobility Separations, Collisional Activation Techniques, and Multiple Stages of MS for Analysis of Complex Peptide Mixtures*", Analytical Chemistry, vol. 74, No. 5, pp. 992-1006, 2002.

Hoaglund et al., "*Ion Trap/Ion Mobility/Quadrupole/Time-of-Flight Mass Spectrometry for Peptide Mixture Analysis*", Analytical Chemistry, vol. 73, No. 2, pp. 177-184, 2001.

Hoaglund et al., "*Mobility Labeling for Parallel CID of Ion Mixtures*", Analytical Chemistry, vol. 72, No. 13, pp. 2737-2740, 2000.

Hoaglund et al., "*Three-Dimensional Ion Mobility/TOFMS Analysis of Electrosprayed Biomolecules*", Analytical Chemistry, vol. 70, No. 1, pp. 2236-2242, 1998.

Valentine et al., "*Developing Liquid Chromatography Ion Mobility Mass Spectrometry Techiques*", Expert Review of Proteomics, vol. 2, No. 4, pp. 553-565, 2005.

Valentine et al., "*Toward Plasma Proteome Profiling with Ion Mobility-Mass Spectrometry*", Journal of Proteome Research, vol. 5, No. 11, pp. 2977-2984, 2006.

* cited by examiner

MULTI-DIMENSIONAL SURVEY SCANS FOR IMPROVED DATA DEPENDENT ACQUISITIONS

CROSS-REFERENCE TO RELATED APPLICATION

This application is the National Stage of International Application No. PCT/GB2013/050595, filed 11 Mar. 2013, which claims priority from and the benefit of United Kingdom Patent Application No. 1205009.2 filed on 22 Mar. 2012. The entire contents of this application is incorporated herein by reference.

BACKGROUND OF THE PRESENT INVENTION

The present invention relates to a method of analysing ions, a method of mass spectrometry, an analytical instrument for analysing ions and a mass spectrometer.

It is known to perform Data Dependent Acquisitions ("DDA") using a mass spectrometer wherein an initial survey scan of parent ions is performed. Once an initial survey scan has been performed, parent ions of interest are determined and are then isolated or selected by a quadrupole mass filter. The parent ions of interest are isolated or selected by arranging for the mass filter to transmit just the specific parent ions of interest on the basis of the mass to charge ratio of the parent ions. The parent ions of interest may then be fragmented and resulting fragment ions may then be mass analysed. Mass analysis of the resulting fragment ions enables the parent ions of interest to be identified or the identity of the parent ions of interest to be confirmed.

Figure 1:
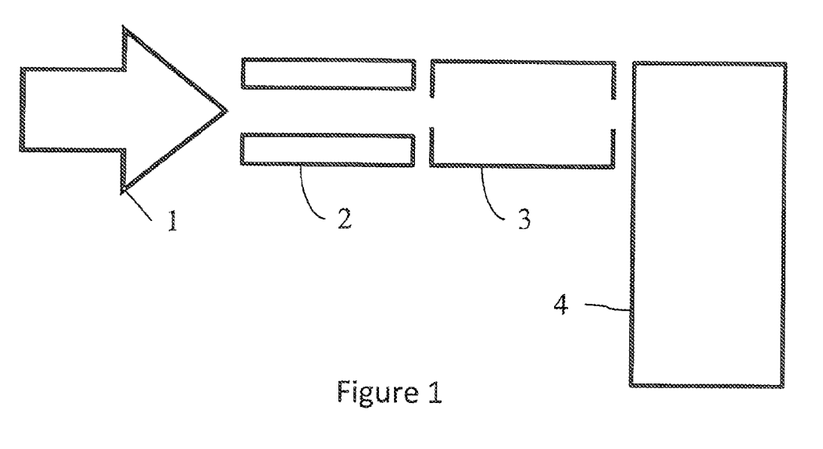
FIG. 1 shows a known quadrupole-Time of Flight mass spectrometer which may be utilised to perform a DDA experiment.

FIG. 1 shows a known arrangement comprising a quadrupole-Time of Flight mass spectrometer which may be used to perform conventional DDA experiments. Ions from an ion source 1 are transmitted to a quadrupole rod set mass filter 2. A gas collision or fragmentation cell 3 is located downstream of the quadrupole mass filter 2 and an orthogonal acceleration Time of Flight mass analyser 4 is located downstream of the gas collision or fragmentation cell 3.

An initial survey scan may be performed wherein the quadrupole 2 is operated in an ion guiding only mode of operation so that a wide range of precursor or parent ions are onwardly transmitted by the quadrupole 2 to the gas cell 3. The gas cell 3 is also operated in an ion guide only mode of operation (i.e. in a non-fragmenting mode of operation) so that a wide mass to charge range of parent ions are onwardly transmitted to the orthogonal acceleration Time of Flight mass analyser 4 without causing the parent ions to be fragmented. The precursor or parent ions are then mass analysed by the orthogonal acceleration Time of Flight mass analyser 4.

The mass to charge ratio of parent ions of interest as derived from the initial survey scan is then used to control the subsequent operation of the quadrupole mass filter 2 based upon user defined rules.

The quadrupole mass filter 2 is operated so as to sequentially isolate or select specific precursor or parent ions of interest. The parent ions of interest which are onwardly transmitted by the mass filter 2 are then accelerated into the gas cell 3 so as to cause the precursor or parent ions to fragment. The resulting fragment ions are then onwardly transmitted to the orthogonal acceleration Time of Flight mass analyser 4 for subsequent mass analysis.

Fragment ions may be assigned to or correlated with precursor or parent ions with a level of confidence due to the selectivity of the mass filtering stage.

Whilst this approach has proven useful, it is not without drawbacks.

Firstly, the known approach suffers from the problem of having a relatively low duty cycle since a plurality of species of parent ions will arrive at the quadrupole mass filter 2 at substantially the same time but only a single species of parent ions of interest will be onwardly transmitted by the mass filter 2. The other parent ions of interest will be attenuated by the mass filter 2.

Secondly, the known approach can exhibit insufficient selectivity of the isolation step when processing complex mixtures. The latter problem is known as chimeracy. For example, two different species of parent ions may have substantially the same mass to charge ratio. However, the quadrupole mass filter 2 will transmit both species of parent ion since it is unable to distinguish between the two different species of ions.

The first problem of reduced duty cycle arises as a result of the sequential temporal nature of the mass filtering step in conventional DDA experiments. By way of illustration, if the initial survey scan identifies ten precursor or parent ions of interest which are desired to be selected and onwardly transmitted by the mass filter 2, then the quadrupole mass filter 2 will be arranged to select each of the ten different precursor or parent ions individually and in turn. Whilst a particular precursor or parent ion is being isolated or selected the other nine species of precursor or parent ions (by virtue of the fact that they are present in the quadrupole mass filter 2 at the same time) are lost to the quadrupole mass filter 2. As a result, the precursor or parent ion selection duty cycle is only 10%.

The second problem of insufficient isolation or selectivity arises from the fact that multiple precursor or parent ion species may be onwardly transmitted by the quadrupole mass filter 2 during a single isolation stage. This can be due to the limited mass resolution or mass transmission window of the quadrupole mass filter 2 or it can be due to two or more species of precursor or parent ions having substantially the same mass to charge ratio being present at the same time (i.e. an isobaric interference).

It is desired to provide an improved mass spectrometer and method of mass spectrometry.

SUMMARY OF THE PRESENT INVENTION

According to an aspect of the present invention there is provided a method of analysing ions comprising:

performing an initial multi-dimensional survey scan comprising separating parent ions according to a first physico-chemical property and separating the parent ions according to a second physico-chemical property;

determining a plurality of parent ions of interest from the initial multi-dimensional survey scan; and then sequentially selecting and transmitting the plurality of parent ions of interest based upon the first physico-chemical property and/or the second physico-chemical property during a single acquisition or cycle of separation; and analysing either: (i) the one or more parent ions of interest; and/or (ii) one or more fragment, product or other ions derived from the one or more parent ions of interest.

It will be understood by those skilled in the art that conventional DDA experiments involve performing an initial survey scan which essentially separates parent or precursor ions in one dimension only (i.e. mass to charge ratio)

by transmitting the parent or precursor ions to an orthogonal acceleration Time of Flight mass analyser which then mass analyses the parent or precursor ions.

In contrast, according to a preferred embodiment of the present invention a multi-dimensional survey scan is initially performed. According to the preferred embodiment parent ions are preferably separated according to a first physico-chemical property (e.g. ion mobility) by a first separator (e.g. an ion mobility separator) and are also then separated according to a second physico-chemical property (e.g. mass or mass to charge ratio) by a second separator (e.g. an orthogonal acceleration Time of Flight mass analyser) during the initial survey can.

According to the preferred embodiment multiple different species of parent ions are then sequentially selected or otherwise isolated on the basis of their first and/or second physico-chemical properties during a single experimental run, acquisition or cycle of separation. This is in contrast to the conventional method of performing a DDA experiment wherein only a single species of parent ion is selected per experimental run or acquisition.

As a result, the method according to the preferred embodiment results in a significant improvement in duty cycle.

The method of mass spectrometry according to the preferred embodiment improves the duty cycle of the precursor or parent ion selection stage in a Data Dependent Acquisition ("DDA") experiment and/or preferably improves the specificity of the individual isolation steps.

The preferred embodiment provides the capability to separate and measure precursor or parent ions according to two (or more) characteristics that preferably have some degree of orthogonality such as ion mobility and mass to charge ratio. Precursor or parent ions are preferably selected or isolated in both dimensions before being onwardly transmitted. The precursor or parent ions may optionally be fragmented and either the parent or precursor ions or fragment or product ions derived from the parent or precursor ions may then be mass analysed by a Time of Flight or other mass analyser.

The two or more dimensional separation of the ions advantageously results in improved specificity of the precursor or parent ions (or resulting fragment ions), improved isolation (i.e. reduced chimeracy) and significantly improved duty cycle compared to conventional mass spectrometers and conventional modes of operation.

According to the preferred embodiment the first physico-chemical property comprises ion mobility or differential ion mobility.

According to another embodiment the first physico-chemical property comprises mass, mass to charge ratio or time of flight.

According to an embodiment the second physico-chemical property comprises ion mobility or differential ion mobility.

According to the preferred embodiment the second physico-chemical property comprises mass, mass to charge ratio or time of flight.

The step of separating ions according to the first physico-chemical property preferably comprises separating ions temporally.

The step of separating ions according to the second physico-chemical property preferably comprises separating ions temporally.

According to a less preferred embodiment the step of separating ions according to the first physico-chemical property comprises separating ions spatially.

According to a less preferred embodiment the step of separating ions according to the second physico-chemical property comprises separating ions spatially.

The step of selecting the plurality of parent ions of interest preferably comprises separating or filtering the parent ions according to the first physico-chemical property and filtering the parent ions according to the second physico-chemical property.

The step of selecting the plurality of parent ions of interest preferably comprises separating or filtering the parent ions according to the first physico-chemical property which preferably comprises ion mobility or differential ion mobility.

According to a preferred embodiment the method further comprises using an ion mobility or differential ion mobility separator to separate the parent ions according to their ion mobility or differential ion mobility.

The step of selecting the plurality of parent ions of interest preferably comprises filtering the parent ions according to the second physico-chemical property which preferably comprises mass, mass to charge ratio or time of flight.

According to a preferred embodiment the method further comprises using a quadrupole rod set mass filter to filter the parent ions according to their mass, mass to charge ratio or time of flight.

The step of selecting the plurality of parent ions of interest based upon the first physico-chemical property and/or the second physico-chemical property during a single acquisition or cycle of separation preferably comprises using a quadrupole rod set mass filter to filter ions according to the second physico-chemical property which preferably comprises mass, mass to charge ratio or time of flight.

The method preferably further comprises applying a broadband excitation voltage to the mass filter in order to attenuate or reject ions having a range of masses or mass to charge ratios and wherein the broadband excitation voltage preferably includes one or more frequency notches so that ions having specific desired masses or mass to charge ratios are not substantially attenuated or rejected by the mass filter.

According to a preferred embodiment the method preferably further comprises attenuating ions in a time dependent manner in order to prevent saturation of an ion detector.

According to a preferred embodiment the method further comprises after the step of selecting one or more parent ions of interest causing the one or more parent ions of interest to fragment or react so as to form fragment or product ions.

The first physico-chemical property and the second physico-chemical property may be the same and/or may be substantially correlated.

Alternatively, the first physico-chemical property and the second physico-chemical property may be substantially different and/or may be substantially uncorrelated.

According to an embodiment the method further comprises increasing the spatial distribution of one or more of the parent ions of interest and/or one or more fragment, product or other ions derived from the one or more parent ions of interest after the one or more parent ions have been sequentially selected and transmitted and prior to the step of analysing either: (i) the one or more parent ions of interest; and/or (ii) one or more fragment, product or other ions derived from the one or more parent ions of interest. Increasing the spatial distribution of the ions prior to the mass analysis step is particularly advantageous in the context of orthogonal acceleration Time of Flight mass analysis since it enables the parent or other ions of interest to be sampled by a greater number of pusher events or time of flight separations. This is advantageous since it enables the ion peak to be analysed with a greater resolution and the intensity of ions being detected in any single pusher event will be reduced with the advantage that the ion detector is less likely to suffer from saturation effects.

According to an aspect of the present invention there is provided a method of mass spectrometry, comprising a method as described above.

According to an aspect of the present invention there is provided an analytical instrument for analysing ions comprising:

a first separator or filter for separating or filtering ions according to a first physico-chemical property;

a second separator or filter for separating or filtering ions according to a second physico-chemical property;

an analyser; and a control system arranged and adapted:

(i) to perform an initial multi-dimensional survey scan comprising separating parent ions according to the first physico-chemical property using the first separator and separating the parent ions according to the second physico-chemical property using the second separator;

(ii) to determine a plurality of parent ions of interest from the initial multi-dimensional survey scan; and then (iii) to sequentially select and transmit the plurality of parent ions of interest based upon the first physico-chemical property and/or the second physico-chemical property during a single acquisition or cycle of separation; and (iv) to cause the analyser to analyse either: (i) the one or more parent ions of interest; and/or (ii) one or more fragment, product or other ions derived from the one or more parent ions of interest.

According to an aspect of the present invention there is provided a mass spectrometer comprising an analytical instrument as described above.

According to an aspect of the present invention there is provided a method of analysing ions comprising:

performing an initial multi-dimensional survey scan comprising separating parent ions according to a first physico-chemical property and separating the parent ions according to a second physico-chemical property;

determining a plurality of parent ions of interest from the initial multi-dimensional survey scan; and then fragmenting the parent ions to generate a plurality of first generation fragment ions;

sequentially selecting and transmitting a plurality of first generation fragment ions of interest based upon the first physico-chemical property and/or the second physico-chemical property during a single acquisition or cycle of separation;

fragmenting the plurality of first generation fragment ions of interest to generate a plurality of second generation fragment ions; and analysing either: (i) the second generation fragment ions; and/or (ii) fragment, product or other ions derived from the second generation fragment ions.

The step of selecting a plurality of first generation fragment ions of interest preferably comprises selecting first generation fragment ions on the basis of the first physico-chemical property of corresponding parent ions, wherein the first physico-chemical property preferably comprises ion mobility or differential ion mobility.

The step of selecting a plurality of first generation fragment ions of interest preferably comprises selecting first generation fragment ions on the basis of the second physico-chemical property of the first generation fragment ions, wherein the second physico-chemical property preferably comprises mass, mass to charge ratio or time of flight.

According to an aspect of the present invention there is provided a mass spectrometer comprising:

a first separator or filter for separating or filtering ions according to a first physico-chemical property;

a second separator or filter for separating or filtering ions according to a second physico-chemical property;

a fragmentation device; and a control system arranged and adapted:

(i) to perform an initial multi-dimensional survey scan comprising separating parent ions according to the first physico-chemical property and separating the parent ions according to the second physico-chemical property;

(ii) to determine a plurality of parent ions of interest from the initial multi-dimensional survey scan; and then (iii) to cause the parent ions to fragment within the fragmentation device to generate a plurality of first generation fragment ions;

(iv) to sequentially select and transmit a plurality of first generation fragment ions of interest based upon the first physico-chemical property and/or the second physico-chemical property during a single acquisition or cycle of separation;

(v) to cause the plurality of first generation fragment ions of interest to fragment to generate a plurality of second generation fragment ions; and (vi) to analyse either: (i) the second generation fragment ions; and/or (ii) fragment, product or other ions derived from the second generation fragment ions.

According to an aspect of the present invention there is provided a method of analysing ions comprising:

performing an initial survey scan comprising separating parent ions according to one or more physico-chemical properties;

determining a plurality of parent ions of interest from the survey scan; and then sequentially selecting and transmitting the plurality of parent ions of interest based upon the one or more physico-chemical properties during a single acquisition or cycle of separation; and analysing either: (i) the one or more parent ions of interest; and/or (ii) one or more fragment, product or other ions derived from the one or more parent ions of interest.

According to an aspect of the present invention there is provided a mass spectrometer comprising:

one or more separators for separating ions according to one or more physico-chemical properties; and a control system arranged and adapted:

(i) to perform an initial survey scan comprising separating parent ions according to the one or more physico-chemical properties in the one or more separators;

(ii) to determine a plurality of parent ions of interest from the survey scan; and then (iii) to sequentially select and transmit the plurality of parent ions of interest based upon the one or more physico-chemical properties during a single acquisition or cycle of separation; and (iv) to analyse either: (a) the one or more parent ions of interest; and/or (b) one or more fragment, product or other ions derived from the one or more parent ions of interest.

According to another aspect of the present invention there is provided a method of screening a sample to determine whether or not specific ions of interest are present in the sample comprising:

separating or filtering parent ions according to a first physico-chemical property and separating or filtering the parent ions according to a second physico-chemical property;

sequentially selecting and onwardly transmitting one or more specific parent ions of interest if the one or more parent ions of interest have a specific predetermined first physico-chemical property and a specific predetermined second physico-chemical property during a single acquisition or cycle of separation, wherein other parent ions having the same charge state as the one or more specific parent ions of interest are substantially attenuated; and analysing either: (i) the one or more specific parent ions of interest; and/or (ii) one or more fragment, product or other ions derived from the one or more specific parent ions of interest.

According to this approach an initial multi-dimensional survey scan is preferably not performed during the same acquisition. Instead, the details of how specific parent ions of interest separate in two dimensions of separation is stored and utilised as a method development step. The predetermined method development step is then used to monitor for the presence of the specific parent ions of interest which might, for example, comprise impurities in a food or pharmaceutical sample.

The step of selecting and onwardly selecting specific parent ions of interest having a specific predetermined second physico-chemical property preferably comprises selecting parent ions having a mass or mass to charge ratio within a specific (narrow) mass or mass to charge ratio range e.g. ions having a mass to charge ratio within a range of 1 Da, <1 Da, <0.9 Da, <0.8 Da, <0.7 Da, <0.6 Da, <0.5 Da, <0.4 Da, <0.3 Da, <0.2 Da or <0.1 Da of a specific mass or mass to charge ratio.

Furthermore, specific parent ions of interest are preferably selected and are onwardly transmitted from amongst other parent ions having the same charge stage (which are preferably attenuated).

The first physico-chemical property preferably comprises ion mobility or differential ion mobility.

The second physico-chemical property preferably comprises mass or mass to charge ratio.

The method preferably further comprises additionally separating the parent ions according to a third physico-chemical property.

The third physico-chemical property preferably comprises chromatographic elution time or retention time.

The step of sequentially selecting and onwardly transmitting specific parent ions of interest preferably further comprises onwardly transmitting the specific parent ions of interest if the parent ions of interest also have a specific predetermined third physico-chemical property.

According to another aspect of the present invention there is provided a mass spectrometer comprising:

a first separator or filter for separating or filtering parent ions according to a first physico-chemical property and a second separator or filter for separating or filtering the parent ions according to a second physico-chemical property; and a control system arranged and adapted:

(i) to sequentially select and onwardly transmit one or more specific parent ions of interest if the parent ions of interest have a specific predetermined first physico-chemical property and a specific predetermined second physico-chemical property during a single acquisition or cycle of separation, wherein other parent ions having the same charge state as the one or more parent ions of interest are substantially attenuated; and (ii) to analyse either: (a) the one or more specific parent ions of interest; and/or (b) one or more fragment, product or other ions derived from the one or more specific parent ions of interest.

The first physico-chemical property preferably comprises ion mobility or differential ion mobility.

The second physico-chemical property preferably comprises mass or mass to charge ratio.

The mass spectrometer preferably comprises a third separator for separating the parent ions according to a third physico-chemical property.

The third physico-chemical property preferably comprises chromatographic elution time or retention time.

According to an embodiment the control system is further arranged and adapted to sequentially select and onwardly transmit specific parent ions of interest if the parent ions of interest also have a specific predetermined third physico-chemical property.

According to the preferred embodiment a mass spectrometer comprising at least two different or separate ion separation devices is provided.

According to an embodiment one of the ion separation devices may comprise an ion mobility spectrometer or separator and the other ion separation device may comprise a mass spectrometer or mass analyser.

According to the preferred embodiment the mass spectrometer preferably comprises at least one ion filter (e.g. a mass filter) that preferably filters or separates ions according to one of the aforementioned characteristics (e.g. mass to charge ratio) and a fragmentation or reaction device for producing product or fragment ions (e.g. a gas collision cell).

BRIEF DESCRIPTION OF THE DRAWINGS

Various embodiments of the present invention will now be described together with an arrangement given for illustrative purposes only by way of example only and with reference to the accompanying drawings in which.

DETAILED DESCRIPTION OF PREFERRED EMBODIMENTS

Figure 2:
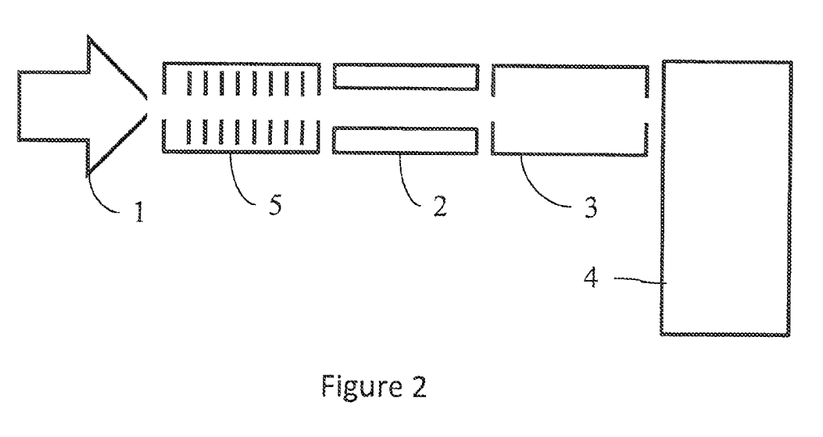
FIG. 2 shows a mass spectrometer according to an embodiment of the present invention comprising an ion mobility separator, a quadrupole mass filter, a gas cell and an orthogonal acceleration Time of Flight mass analyser.

A preferred embodiment of the present invention will now be described with reference to FIG. 2. A mass spectrometer according to an embodiment of the present invention is shown in FIG. 2 and comprises an ion mobility separator 5, a quadrupole mass filter 2, a gas cell 3 and an orthogonal acceleration Time of Flight mass analyser 4. Ions from an ion source 1 are preferably passed to the ion mobility separator 5 and are preferably separated according to their ion mobility within the ion mobility separator 5.

The preferred embodiment seeks to address two problems which are inherent with a conventional method of performing a Data Dependent Acquisition ("DDA") wherein an initial survey scan is performed and parent ions of interest are subsequently selected solely on the basis of their mass to charge ratio by a quadrupole mass filter.

Firstly, in order to improve the otherwise relatively low precursor or parent ion selection duty cycle, according to a preferred embodiment the precursor or parent ions are preferably temporally separated by separating the ions according to their ion mobility in the ion mobility separator 5 prior to the ions being presented to the quadrupole mass filter 2.

According to the preferred embodiment the mass filter 2 is preferably switched so as to onwardly transmit a plurality of different species of precursor or parent ions of interest during a single acquisition, experimental run or cycle of separation. As a result since multiple different species of parent ions of interest are selected and onwardly transmitted by the mass filter 2 without being attenuated during a single cycle of separation then the method according to the present invention results in a significant improvement in duty cycle.

Ideally, the time taken by the mass filter 2 to switch between different precursor or parent ions of interest is significantly shorter than the pre-separation time in the ion mobility spectrometer 5 and this allows the possibility of switching the mass filter 2 so as to select between multiple different species of precursor or parent ions of interest within each cycle of separation of the ion mobility spectrometer 5 with a resulting high duty cycle.

Secondly, in order to improve chimeracy issues the ion mobility spectrometer 5 or other separation device preferably separates ions based on a characteristic that preferably has some degree of orthogonality to that of the mass filter 2 or other filtering device which preferably separates according to mass to charge ratio.

The pre-separation device, ion mobility separator 5 or other separation device is preferably arranged to separate ions based on a characteristic which is substantially orthogonal to mass or mass to charge ratio i.e. which is uncorrelated with mass to charge ratio.

However, according to other embodiments the pre-separation device may perform separations that are correlated with mass or mass to charge ratio at least to some extent since if there is at least some degree of orthogonality then this will enable a degree of resolution of chimeric ions.

It should be understood that although it is desirable that the separator (e.g. on mobility separator 5) and the filter (e.g. mass filter 2) preferably separate and then filter ions in a substantially orthogonal manner, that it is not essential that the separation and filtering steps are actually orthogonal or indeed have any degree of orthogonality.

According to a less preferred embodiment the separator may separate ions according to their mass, mass to charge ratio or ion mobility with a first (low) resolution and the filter may also filter the ions according to their mass, mass to charge ratio or ion mobility but with a second different (higher) resolution.

According to an embodiment ions 1 exiting an ion source region may be periodically accumulated and then released into the ion mobility separator 5 or other separation device. The ion mobility separator 5 preferably separates the ions in time according to their ion mobility.

An initial survey scan according to the preferred embodiment is preferably performed wherein the ions are preferably onwardly transmitted through a quadrupole mass filter 2 which is preferably operated in a wide mass range mode (i.e. the mass filter 2 does not filter ions according to their mass to charge ratio). The ions then preferably enter a gas collision cell 3 or other fragmentation device which is preferably substantially switched OFF. The gas collision cell 3 or other fragmentation device therefore preferably operates essentially as an ion guide and preferably maintains the fidelity of the ion mobility separation. Unfragmented parent ions preferably exit the gas collision cell 3 and are then transmitted to an orthogonal acceleration Time of Flight mass analyser 4 for subsequent mass analysis.

The Time of Flight mass analyser acquisition system preferably acquires a two-dimensional nested data set where one dimension or axis preferably corresponds to mass to charge ratio (i.e. time of flight through the Time of Flight mass analyser 4) and the other dimension preferably corresponds to ion mobility (due to the temporal separation of ions according to their ion mobility as they pass through the ion mobility separator 5).

Once an initial survey scan has been completed and a two-dimensional nested data set has been obtained, precursor or parent ions of interest are then preferably identified or otherwise determined for subsequent isolation or selection within the two dimensional space.

Figure 3:
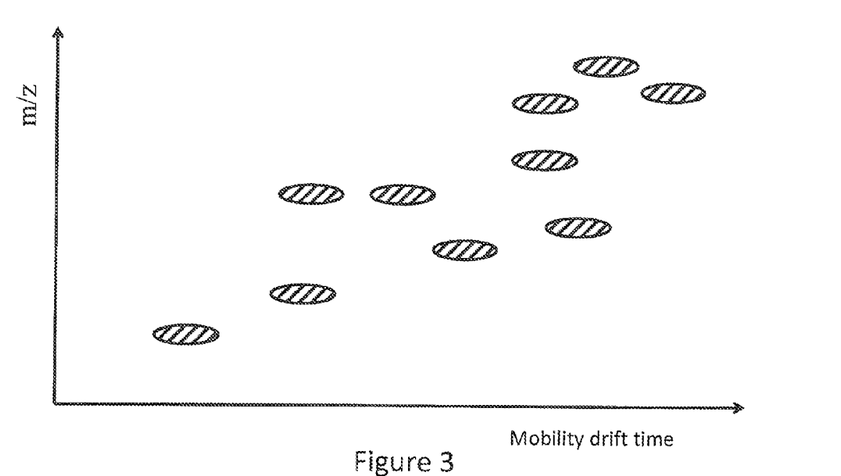
FIG. 3 shows a schematic of an initial two dimensional survey scan according to an embodiment of the present invention which comprises a two dimensional nested data set wherein ions are separated in one dimension according to their ion mobility and are separated in a second dimension according to their mass to charge ratio.

FIG. 3 shows an example of a two dimensional nested data set which may be obtained as a result of an initial survey scan according to the preferred embodiment.

The initial survey scan is preferably analysed and multiple different species of precursor or parent ions of interest are then preferably subsequently isolated or selected in sequence in the two-dimensional space during a single acquisition or experimental run. Multiple different species of precursor or parent ions of interest are preferably sequentially isolated or selected during a single acquisition or cycle of separation by transmitting the precursor or parent ions through the ion mobility separator 5 so as to separate the ions temporally according to their ion mobility. The quadrupole rod set mass filter 2 is then preferably operated so as to sequentially select and onwardly transmit multiple different desired species of precursor or parent ions having specific mass or mass to charge ratios as the precursor or parent ions of interest elute from the on mobility separator 5 during a single cycle of separation of the ion mobility separator 5. Other precursor or parent ions which were not identified as being of interest from the initial survey scan are not onwardly transmitted by the mass filter 2 and are substantially attenuated by the mass filter 2 during the cycle of separation.

Figure 4:
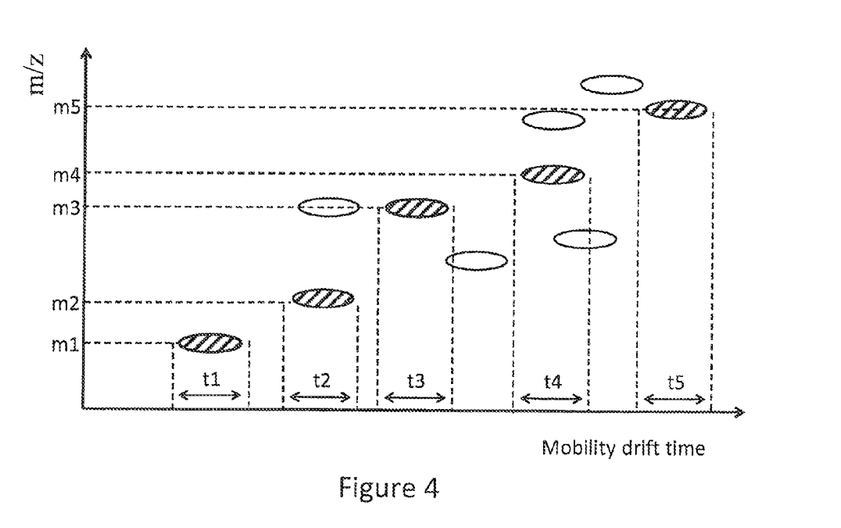
FIG. 4 shows a schematic of an embodiment of the present invention wherein five different species of parent ions within the two dimensional nested data set as shown in FIG. 3 are sequentially isolated or otherwise selected with the result that the duty cycle is significantly improved compared to conventional methods of DDA analysis.

Multiple different species of precursor or parent ions of interest which are preferably isolated or otherwise selected within or during a single mobility separation, single acquisition or single cycle of separation are shown in FIG. 4 wherein the shaded regions correspond with different species of parent or precursor ions of interest which are desired to be isolated or otherwise selected and subsequently analysed.

Parent ions which are not of interest are shown in FIG. 4 as non-shaded regions. These parent ions are not selected by the mass filter 2 for further analysis and are preferably attenuated by the mass filter 2.

According to the preferred embodiment the mass filter 2 is preferably arranged to transmit the parent or precursor ions of interest and to attenuate the other undesired parent or precursor ions.

In the particular example shown in FIG. 4, the mass filter 2 is arranged so as to transmit parent ions having a mass to charge ratio m1 at a time t1, parent ions having a mass to charge ratio m2 at a time t2, parent ions having a mass to charge ratio m5 at a time t3, parent ions having a mass to charge ratio m4 at a time t4 and parent ions having a mass to charge ratio m5 at a time t5.

At other times the mass filter 2 is preferably arranged so as not to onwardly transmit any parent ions i.e. the mass filter 2 is arrange to attenuate all other parent ions.

Also, a time t1 the mass filter 2 is only arranged to transmit parent ions having a mass to charge ratio m1. Similarly, at time t2 only parent ions having a mass to charge ratio m2 are transmitted and at time t3 only parent ions having a mass to charge ratio m3 are transmitted. At time t4 only parent ions having a mass to charge ratio m4 are transmitted and at time t5 only parent ions having a mass to charge ratio m5 are transmitted.

The unshaded regions shown in FIG. 4 represent precursor or parent ions as shown in FIG. 3 which are not of interest and which are not therefore subsequently isolated or selected for subsequent fragmentation or further analysis.

In the particular example shown in FIG. 4 five different species of precursor or parent ions (out of a total of ten different species of precursor or parent ions) are determined to represent parent ions of interest and are as a result sequentially isolated and selected by the mass filter 2 as the parent ions of interest progressively elute from the ion mobility spectrometer 5. As a result, the duty cycle according to this approach is significantly improved by a factor of ×5 compared with the conventional approach wherein only a single species of parent ions of interest is selected for subsequent fragmentation and mass analysis per acquisition.

FIG. 4 also illustrates another advantage of the preferred embodiment in the situation when two different species of parent ions are present having substantially the same mass to charge ratio m3.

According to a conventional method both species of parent ions having a mass to charge ratio m3 would be simultaneously onwardly transmitted by the quadrupole mass filter 2. As a result, this would give rise to a chimeracy issue.

However, according to the preferred embodiment the chimeracy issue is resolved since although the two different species of parent ions have essentially the same mass to charge ratio m3, they emerge from the ion mobility spectrometer 5 at different times. As a result, the species of parent ions of interest having a mass to charge ratio m3 and an ion mobility drift time of t3 can be isolated or selected by the mass filter 2 and be onwardly transmitted to the gas cell 3 whilst the other undesired species of parent ions having a mass to charge ratio m3 but a shorter ion mobility drift time t2 can be arranged to be rejected or otherwise attenuated by the mass filter 2.

A preferred embodiment of the present invention has been described above and relates to separating ions according to their ion mobility and then filtering the ions according to their mass to charge ratio. However, the present invention extends more broadly to covering embodiments comprising a first separator or filter which is arranged and adapted to separate or filter ions according to a first physico-denial property and a second filter which is arranged and adapted to filter ions according to a second physico-chemical property.

If the first and second physico-chemical properties are not strongly connected or otherwise correlated then interferences can be resolved.

Parent or precursor ions of interest which are isolated or selected by the mass filter 2 are preferably arranged to exit the quadrupole mass filter 2 and are then preferably accelerated into a gas collision cell 3 or other fragmentation or reaction device in order to induce the parent ions to fragment or react. The gas collision cell 3 or other fragmentation or reaction device preferably acts to both fragment the parent or precursor ions of interest whilst at the same time maintaining the same separation of fragment ions as corresponding precursor or parent ions separated by the ion mobility separator 5.

The resulting fragment or product ions are then preferably onwardly transmitted to an orthogonal acceleration Time of Flight mass analyser 4 for subsequent mass analysis.

The cycle can be repeated numerous times and the results of multiple two-dimensional separations may preferably be summed.

Figure 5:
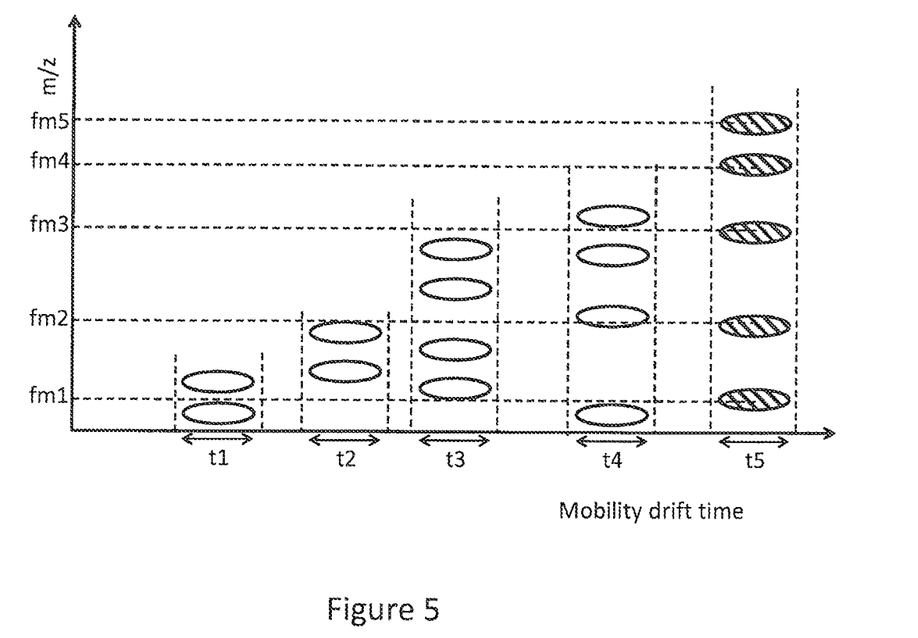
FIG. 5 shows how multiple different species of fragment ions relating to the five different species of parent ions which were selected may be interrogated according to an embodiment of the present invention.

Fragment ion spectra for multiple precursor or parent ions may also be interrogated as the fragment ion spectra are also separated along the ion mobility acquisition axis or dimension as illustrated in FIG. 5. For example, in FIG. 5 five highlighted fragment ions having mass to charge ratios fm1, fm2, fm3, fm4, fm5 are all associated with a specific corresponding precursor or parent ion having an ion mobility drift time t5 and a mass to charge ratio m5 as shown in FIG. 4 (since the fragment ions fm1-fm5 will all observed at essentially the same time t5 as that when the corresponding precursor or parent ion elutes from the on mobility separator 5).

According to the preferred embodiment different types of on mobility separators may be used to separate one according to their ion mobility. According to an embodiment the ion mobility separator may comprise an ion mobility separator having an uniform field, a travelling wave ion mobility spectrometer wherein one or more transient DC voltages or potentials are applied to a plurality of electrodes in order to urge ions along the length of the ion mobility spectrometer, an ion mobility spectrometer wherein ions follow a spiral or helical ion path or a multi-pass ion mobility spectrometer.

According to yet further embodiments the ion mobility spectrometer may comprise an ion funnel and/or a device without pre-accumulation of ions.

The ion mobility spectrometer may be operated over a wide range of pressures and/or may utilise directional gas flows.

Different gas cells may be employed to maintain the fidelity of the mobility separation axis including gas cells or fragmentation devices, wherein ions are translated along the axial length of the gas cell or fragmentation device by one more transient DC voltages or travelling waves and/or by an axial DC electric field.

Other types of mass spectrometers may be used other than a Time of Flight mass analyser. However, a Time of Flight mass analyser is particularly preferred since the separation timescales of Time of Flight mass analysers are fast enough to keep up with ion mobility separation timescales.

The identification of precursor or parent ions for isolation may include criteria such as the degree of separation from other identified precursor or parent ions.

The order in which precursor or parent ions of interest are isolated or otherwise selected may be optimised for short pre-separation cycle times.

It is important to recognise that the duty cycle improvement which is achieved according to the present invention may also be realised without the two-dimensions of separation necessarily being orthogonal. For example, according to an embodiment both dimensions could be mass, mass to charge ratio, ion mobility or differential ion mobility. The improvement in duty cycle which is achieved according to the present invention is achieved by being able to isolate and select multiple different species of parent ions of interest during a single cycle of separation of the separator or during a single acquisition preferably without losing or attenuating any parent ions of interest.

It will be apparent, therefore, that some benefit in duty cycle may be gained even with strongly correlated separations and according to an embodiment a one-dimensional initial survey scan might be performed in some circumstances. In this geometry or mode of operation a measurement in one axis may be used to restrict the range of the other axis. For example, with an IMS-quadrupole-Time of Flight mass spectrometer as shown in FIG. 2 the survey scan may be operating solely in mass to charge ratio. As a result, a strong correlation of mass to charge ratio with IMS drift time will mean that for a given mass to charge ratio and for a particular charge state the range of possible times that parent ions of interest will exit the ion mobility separator is significantly reduced. The mass filter may be switched to transmit the ions at times during these time intervals again providing improved duty cycle and some degree of improved resolution of chimeracy.

The preferred mode of operation may also be used in conjunction with other described modes of operation such as a charge state stripping mode of operation as described in U.S. Pat. No. 7,586,088 (the contents of which are incorporated herein by reference) as well as enhanced Time of Flight duty cycle modes such as an Enhanced Duty Cycle ("EDC") mode of operation and a High Duty Cycle ("HDC") mode of operation.

According to less preferred embodiments the approach described above which is concerned with improving the duty cycle and enhancing specificity may also be adapted to be used with Data Independent Acquisitions ("DIA") or target experiments such as Multiple Reaction Monitoring ("MRM") wherein precursor or parent ions of interest are identified as part of a method development stage as opposed to a DDA initial survey scan.

The mass spectrometer and method of mass spectrometry according to an embodiment of the present invention may include geometries and modes of operation wherein the fidelity of the ion mobility separation is not maintained through to the final stage of the mass spectrometer or mass analyser. For example, multiplexed DDA or MRM modes available on known instruments would benefit from a pre-separation prior to the quadrupole mass filter. The benefit is manifested as both improved duty cycle and improved resolution of chemericy.

A device according to the preferred embodiment may be proceeded by other analytical devices such as mass filters or ion traps.

Timescales permitting, multiple devices may be cascaded together in a parallel or serial manner.

According to an embodiment more than two-dimensions of separation and/or filtering may be used. For example, according to an embodiment ions may be separated and/or filtered in three, four, five or more than five different dimensions.

It is recognised that the multidimensional survey scan according to the preferred embodiment has inherent benefits for separation of interferences offering the potential for improved mass accuracy of the survey scan data and that such benefits are independent of the ability to be able to increase the duty cycle of selecting and analysing parent ions of interest during a single acquisition or cycle of separation.

Other combinations of separators may also benefit from the approach according to the preferred embodiment. For example, filtering mobility devices such as differential mobility separators, FANS and differential mobility analysers combined with a mass filter and/or a Time of Flight mass analyser may be used as they would also benefit from this approach when determining the best time to set the mobility filter and the quadrupole filter.

Other combinations not including a mass spectrometer may also benefit such as Differential Mobility Analyser ("DMA")-IMS instruments.

According to an embodiment the separator may comprise an ion mobility spectrometer such as a drift tube or travelling wave ion mobility spectrometer. The separator may be followed by an ion mobility filter such as a differential ion mobility spectrometer or separator ("DMS"), a Field Asymmetric Ion Mobility Spectrometry ("FAIMS") device or a differential ion mobility analyser ("DMA") device. The same general principle as described above applies and the ion mobility filter may be set to transmit ions at different times within a single on mobility spectrometer cycle or within a single cycle of separation. Such an approach again helps to remove chimeric interferences and improves the duty cycle of the filter.

An embodiment is contemplated wherein a relatively low resolution ion mobility spectrometer may be followed by a differential mobility analyser ("DMA"). The DMA device may be automatically scanned synchronously with the IMS cycle time so as to improve the duty cycle of the scanning DMA device.

The ion mobility information can be useful in its own right for determining collisional cross sections and aiding the identification of precursor or parent ions/database searching.

Multi-dimensional survey scans are advantageous in their own right even without leading to a duty cycle improvement since they enable the separation of interferences and provide improved mass accuracy.

Although the preferred embodiment involves the fragmentation of parent or precursor ions, it should be understood that embodiments of the invention are also contemplated wherein: the parent or precursor ions are not necessarily fragmented. For example, an embodiment of the present invention may relate to a Selected Ion Recording ("SIR") type experiment. According to this embodiment parent ions of interest are not fragmented and a SIR type experiment is performed.

Embodiments of the present invention are also contemplated wherein the intensities of ions are attenuated when separated or after separation. For example, ions may all be attenuated by the same factor or alternatively ions may be attenuated by different factors for different parent or precursor ions.

According to a further embodiment the first separator and/or the second filter and/or optionally a collision or fragmentation device may be provided as part of a closed loop type geometry. According to this embodiment ions are preferably circulated around a closed loop and preferably the first separator (e.g. ion mobility spectrometer) and/or the filter (e.g. quadrupole mass filter) and/or the collision or fragmentation cell are preferably provided within the loop.

According to an embodiment switching or selecting decisions may be based on measurement of either or both of the separation dimensions. For example, ions may be selected on the basis of having a certain characteristic ion mobility or ion mobilities within a certain range, as well as, or in addition to having certain mass to charge ratios.

According to an embodiment ions may be attenuated at any point along the beam path after the separation stage (e.g. ion mobility separation). The attenuation value may be varied within the timescales of the separation (e.g. ion mobility separation) to prevent target ions, parent ions of interest or fragment or product ions derived from the parent ions of interest from saturating the ion detector or from causing other undesirable effects. The attenuation values may be determined from previously acquired data. Such an embodiment is particularly applicable to MRM type acquisitions but also has utility for DDA modes of operation.

According to another embodiment first generation fragment ions from mobility separated parent or precursor ions are preferably isolated or otherwise selected. The first generation fragment ions may then be subjected to further fragmentation to generate second generation fragment ions thereby allowing a $MS^3$ or MS/MS/MS mode of operation in a DDA or targeted mode to be performed. The resulting mass spectral data may then be scaled to correct for the attenuation of the ions so that ions are correctly quantified or quantitated.

According to another embodiment the method or approach according to the preferred embodiment may be used simply to isolate fragment ions related to parent or precursor ions with a higher duty cycle. For example, a peptide or other complex molecule may be fragmented into a plurality of different parent ions having different charge states, having different adducts or having different modifications. The method according to the preferred embodiment enables parent ions having the same characteristics and/or modifications and/or properties to be isolated and selected.

According to another embodiment the data may be simplified in a targeted manner according to the preferred embodiment followed by deliberate loss of IMS separation and fragmentation to produce simplified MS/MS spectra with high dynamic range. In particular, parent ions of interest may emerge from the separator (e.g. ion mobility separator) with a relatively short spread of drift times. Presenting a large intensity of parent ions of interest or related fragment ions to the mass analyser in a short period of time might cause the ion detector to saturate and result in limited resolution of the ion mobility. According to an embodiment the ion mobility peaks may be broadened with the result that parent ions of interest or related fragment ions are now presented to the mass analyser over a longer period of time thereby preventing the ion detector from saturating. Increasing the temporal spread of ions prior to mass analysis will mean that an ion mobility peaks will now be sampled by a greater number of orthogonal acceleration time of flight acquisitions with the result that the resolution of the ion mobility peak shape will be improved.

According to an embodiment a mass filter may be used which utilises a broadband excitation frequency in conjunction with one or more frequency notches as a means of mass filtering ions. This provides an advantage over using a RF/DC resolving quadrupole as multiple mass to charge ratio values or ranges can be transmitted closely spaced in drift time or even simultaneously. This in turn alleviates some of the issues associated with RF/DC switching settling times in the sequential transmission of drift time resolved peaks. It also allows mass to charge ratios ranges overlapping in drift time to be transmitted.

In particular, as an alternative means of providing mass to charge ratio filtration after ion mobility separation, a quadrupole rod set operated with a broadband noise signal for ion rejection may be employed with frequency notches arranged to allow transmission of particular ions of interest. The utility of this approach is that a sequence of single frequency notches can be used for mass filtration during e.g. an ion mobility (or other) separation and/or multiple overlapping frequency notches may be used to onwardly transmit ions having more than one mass to charge ratio at any given drift time. The frequency notches may be relatively narrow so as to admit a single or small mass to charge ratio range or alternatively the frequency notches may be broader so as to cover a range of mass to charge ratios.

In cases where multiple components are overlapping in drift time it may be advantageous to maintain the drift time profile information to aid any subsequent precursor ion assignments. This is applicable to the notch frequency approach as described above and also to the previously described sequential RF/DC method.

Although the present invention has been described with reference to preferred embodiments, it will be understood by those skilled in the art that various changes in form and detail may be made without departing from the scope of the invention as set forth in the accompanying claims.

The invention claimed is:

1. A method of analysing ions in a Data Dependent Acquisition (DDA) experiment comprising:
   performing an initial multi-dimensional survey scan comprising separating parent ions according to a first physico-chemical property and separating said parent ions according to a second physico-chemical property;
   determining a plurality of parent ions of interest to be selected for the DDA experiment from said initial multi-dimensional survey scan; and then
   sequentially selecting and transmitting said plurality of parent ions of interest based upon said first physico-chemical property and said second physico-chemical property during a single acquisition or cycle of separation; and
   analysing either: (i) one or more of said plurality of parent ions of interest; or (ii) one or more fragment, product or other ions derived from one or more of said plurality of parent ions of interest.

2. A method as claimed in claim 1, wherein said first physico-chemical property comprises ion mobility or differential ion mobility.

3. A method as claimed in claim 1, wherein said first physico-chemical property comprises mass, mass to charge ratio or time of flight.

4. A method as claimed in claim 1, wherein said second physico-chemical property comprises ion mobility or differential ion mobility.

5. A method as claimed in claim 1, wherein said second physico-chemical property comprises mass, mass to charge ratio or time of flight.

6. A method as claimed in claim 1, wherein the step of separating ions according to said first physico-chemical property comprises separating ions temporally.

7. A method as claimed in claim 1, wherein the step of separating ions according to said second physico-chemical property comprises separating ions temporally.

8. A method as claimed in claim 1, wherein the step of separating ions according to said first physico-chemical property comprises separating ions spatially.

9. A method as claimed in claim 1, wherein the step of separating ions according to said second physico-chemical property comprises separating ions spatially.

10. A method as claimed in claim 1, wherein the step of selecting said plurality of parent ions of interest comprises separating or filtering said parent ions according to said first physico-chemical property and filtering said parent ions according to said second physico-chemical property.

11. A method as claimed in claim 10, wherein the step of selecting said plurality of parent ions of interest comprises separating or filtering said parent ions according to said first physico-chemical property which comprises ion mobility or differential ion mobility.

12. A method as claimed in claim 11, further comprising using an ion mobility or differential ion mobility separator to separate said parent ions according to their ion mobility or differential ion mobility.

13. A method as claimed in claim 11, wherein the step of selecting said plurality of parent ions of interest comprises filtering said parent ions according to said second physico-chemical property which comprises mass, mass to charge ratio or time of flight.

14. A method as claimed in claim 13, further comprising using a quadrupole rod set mass filter to filter said parent ions according to their mass, mass to charge ratio or time of flight.

15. A method as claimed in claim 1, wherein the step of selecting said plurality of parent ions of interest based upon said first physico-chemical property and said second physico-chemical property during a single acquisition or cycle of separation comprises using a quadrupole rod set mass filter to filter ions according to said second physico-chemical property which comprises mass, mass to charge ratio or time of flight.

16. A method as claimed in claim 15, wherein said method further comprises applying a broadband excitation voltage to said mass filter in order to attenuate or reject ions having a range of masses or mass to charge ratios and wherein said broadband excitation voltage includes one or more frequency notches so that ions having specific desired masses or mass to charge ratios are not substantially attenuated or rejected by said mass filter.

17. A method as claimed in claim 1, further comprising attenuating ions in a time dependent manner in order to prevent saturation of an ion detector.

18. A method as claimed in claim 1, further comprising after the step of selecting one or more parent ions of interest causing said one or more parent ions of interest to fragment or react so as to form fragment or product ions.

19. A method as claimed in claim 1, wherein said first physico-chemical property and said second physico-chemical property are the same or are substantially correlated.

20. A method as claimed in claim 1, wherein said first physico-chemical property and said second physico-chemical property are substantially different or are substantially uncorrelated.

21. A method as claimed in claim 1, further comprising increasing the spatial distribution of one or more of said plurality of parent ions of interest or one or more fragment, product or other ions derived from one or more of said plurality of parent ions of interest after one or more of said plurality of parent ions have been sequentially selected and transmitted and prior to the step of analysing either: (i) one or more of said plurality of parent ions of interest; or (ii) one or more fragment, product or other ions derived from one or more of said plurality of parent ions of interest.

22. A method of mass spectrometry, comprising a method as claimed in claim 1.

23. An analytical instrument for analysing ions in a Data Dependent Acquisition (DDA) experiment comprising:

a first separator or filter for separating or filtering ions according to a first physico-chemical property;

a second separator or filter for separating or filtering ions according to a second physico-chemical property;

an analyser; and a control system arranged and adapted:

(i) to perform an initial multi-dimensional survey scan comprising separating parent ions according to said first physico-chemical property using said first separator and separating said parent ions according to said second physico-chemical property using said second separator;

(ii) to determine a plurality of parent ions of interest to be selected for the DDA experiment from said initial multi-dimensional survey scan; and then (iii) to sequentially select and transmit said plurality of parent ions of interest based upon said first physico-chemical property and said second physico-chemical property during a single acquisition or cycle of separation; and (iv) to cause said analyser to analyse either: (i) one or more of said plurality of parent ions of interest; or (ii) one or more fragment, product or other ions derived from one or more of said plurality of parent ions of interest.

24. A mass spectrometer comprising an analytical instrument as claimed in claim 23.

25. A method of analysing ions in a Data Dependent Acquisition (DDA) experiment comprising:

performing an initial multi-dimensional survey scan comprising separating parent ions according to a first physico-chemical property and separating said parent ions according to a second physico-chemical property;

determining a plurality of parent ions of interest to be selected for the DDA experiment from said initial multi-dimensional survey scan; and then fragmenting said parent ions to generate a plurality of first generation fragment ions;

sequentially selecting and transmitting a plurality of first generation fragment ions of interest based upon said first physico-chemical property and said second physico-chemical property during a single acquisition or cycle of separation;

fragmenting said plurality of first generation fragment ions of interest to generate a plurality of second generation fragment ions; and analysing either: (i) said second generation fragment ions; or (ii) fragment, product or other ions derived from said second generation fragment ions.

26. A method as claimed in claim 25, wherein the step of selecting a plurality of first generation fragment ions of interest comprises selecting first generation fragment ions on the basis of said first physico-chemical property of corresponding parent ions, wherein said first physico-chemical property comprises ion mobility or differential ion mobility.

27. A method as claimed in claim 25, wherein the step of selecting a plurality of first generation fragment ions of interest comprises selecting first generation fragment ions on the basis of said second physico-chemical property of said first generation fragment ions, wherein said second physico-chemical property comprises mass, mass to charge ratio or time of flight.

28. A mass spectrometer for use in a Data Dependent Acquisition (DDA) experiment comprising:

a first separator or filter for separating or filtering ions according to a first physico-chemical property;

a second separator or filter for separating or filtering ions according to a second physico-chemical property;
a fragmentation device; and
a control system arranged and adapted:
(i) to perform an initial multi-dimensional survey scan comprising separating parent ions according to said first physico-chemical property and separating said parent ions according to said second physico-chemical property;
(ii) to determine a plurality of parent ions of interest to be selected for the DDA experiment from said initial multi-dimensional survey scan; and then
(iii) to cause said parent ions to fragment within said fragmentation device to generate a plurality of first generation fragment ions;
(iv) to sequentially select and transmit a plurality of first generation fragment ions of interest based upon said first physico-chemical property and said second physico-chemical property during a single acquisition or cycle of separation;
(v) to cause said plurality of first generation fragment ions of interest to fragment to generate a plurality of second generation fragment ions; and
(vi) to analyse either: (i) said second generation fragment ions; or (ii) fragment, product or other ions derived from said second generation fragment ions.

* * * * *